United States Patent [19]

Kawamata et al.

[11] Patent Number: 5,334,372

[45] Date of Patent: * Aug. 2, 1994

[54] ALCOHOL-MODIFIED SILICON ESTER DERIVATIVE AND COSMETIC COMPOSITION CONTAINING SAME

[75] Inventors: Akira Kawamata, Utsunomiya; Yoko Kikuchi, Toride; Yuji Suzuki, Sakura; Toshiyuki Suzuki, Ichikawa; Mituo Suda; Yukihiro Ohashi, both of Ichikaimachi, all of Japan

[73] Assignee: Kao Corporation, Tokyo, Japan

[*] Notice: The portion of the term of this patent subsequent to May 11, 2010 has been disclaimed.

[21] Appl. No.: 17,996

[22] Filed: Feb. 16, 1993

Related U.S. Application Data

[63] Continuation of Ser. No. 806,790, Dec. 12, 1991, abandoned, which is a continuation of Ser. No. 417,450, Oct. 5, 1989, abandoned.

[30] Foreign Application Priority Data

Oct. 7, 1988 [JP]  Japan .................. 63-252942
Dec. 5, 1988 [JP]  Japan .................. 63-307456
Feb. 27, 1989 [JP]  Japan .................. 1-45795

[51] Int. Cl.$^5$ .................. A61K 31/74; A61K 7/021
[52] U.S. Cl. .................. 424/78.03; 424/63; 424/64; 424/70; 424/71; 514/847
[58] Field of Search .................. 424/70, 71, 78.03, 63, 424/64; 514/772, 844, 847, 846, 937, 938

[56] References Cited

U.S. PATENT DOCUMENTS

| | | | |
|---|---|---|---|
| 3,298,919 | 1/1967 | Bishop et al. | 424/78 X |
| 3,795,634 | 3/1974 | Noelsen | 521/73 |
| 4,782,095 | 11/1988 | Gum | 514/938 X |
| 4,957,732 | 9/1990 | Grollier et al. | 514/792 X |
| 5,210,251 | 5/1993 | Ohashi | 556/437 |

FOREIGN PATENT DOCUMENTS

62-126111  5/1987  Japan .................. A61K 7/060

*Primary Examiner*—Thurman K. Page
*Assistant Examiner*—Sally Gardner
*Attorney, Agent, or Firm*—Oblon, Spivak, McClelland, Maier & Neustadt

[57] ABSTRACT

A novel alcohol-modified silicone ester derivative of the following formula (I):

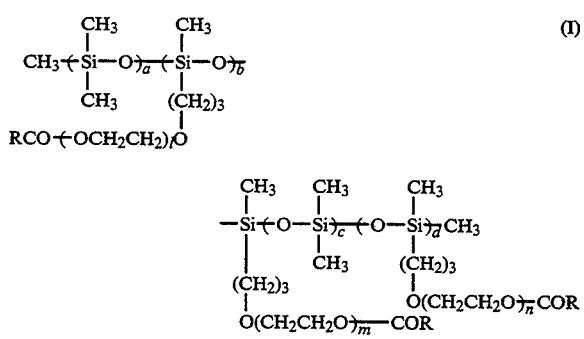

wherein R is a saturated or unsaturated, linear, branched or cyclic aromatic residual or hydrocarbon group; a, b and c are numbers which sum falls in the range from 0 to 130; d is a number lying between 0 and 1; and 1, m and n are numbers which sum falls in the range from 0 to 6.

Cosmetic compositions containing the above silicone ester derivative (I) were also disclosed.

The silicone ester derivative (I) is useful as a cosmetic ingredient due to the capability of improving feel on use.

4 Claims, 12 Drawing Sheets

ALCOHOL-MODIFIED SILICON ESTER DERIVATIVE AND COSMETIC COMPOSITION CONTAINING SAME

This application is a continuation of application Ser. No. 07/806,790, filed on Dec. 12, 1991, now abandoned, which is a continuation of Ser. No. 07/417,450, field Oct. 5, 1989, now abandoned.

BACKGROUND OF THE INVENTION i) Field of the Invention

This invention relates to a novel alcohol-modified silicone ester derivative (hereinafter referred to simply as silicone ester derivative) and cosmetic compositions containing same.

ii) Description of the Background Art

Silicone oils are widely used as an oil ingredient for cosmetic compositions due to their excellent lubricity, water repellency, gloss imparting capability, stability, safety, etc. Among them, a high molecular dimethylpolysiloxane has generally been used in the art. The dimethylpolysiloxane, however, raises a problem when incorporated in a cosmetic composition. It gives disagreeable feel to the skin. In detail, it gives creaky feel when that of low viscosity is used and sticky feel when that of high viscosity is used. Moreover, it is accompanied by an another problem in that an emulsion system is difficult to obtain because the high molecular dimethylpolysiloxane has poor compatibility with hydrocarbon oils.

With regard to the art focusing on the above problem of the high molecular dimethylpolysiloxane, there are two publications which are Japanese patent application laid-open to the public, Kokai 61-129187 and Kokai 63-150288. They disclose esterified products between dimethylpolysiloxanediol and a dibasic acid or between dimethyl polysiloxanediol and a long-chain fatty acid, respectively. These compounds, however, still demand improvement of feel on use and blendability The present invention was made primarily to overcome the above-mentioned drawbacks of the silicone oils by taking an approach quite different from those disclosed in the mentioned publications, and to develop a novel silicone derivative having excellent properties which were never obtained from the conventional silicone oils, and further to develop cosmetic compositions having agreeable feel on use.

The present inventions carried out an earnest study focusing on the above goals and found that an alcohol-modified silicone ether derivative of formula (I) had a good compatibility with other solvents, gave agreeable feel upon use and was free from the drawbacks accompanied by the conventional silicone oils. Such findings have led to the completion of this invention.

SUMMARY OF THE INVENTION

Accordingly, an object of this invention is to provide an alcohol-modified silicone ester derivative represented by the following formula (I):

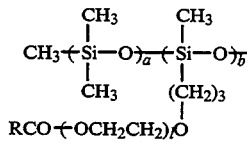

-continued

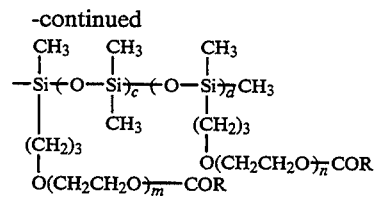

wherein R is a saturated or unsaturated, linear, branched or cyclic aromatic residual or hydrocarbon group; a, b and c are numbers which sum falls in the range from 0 to 130; d is a number lying between 0 and 1; and l, m and n are numbers which sum falls in the range from 0 to 6. Another object of this invention is to provide a cosmetic composition containing the same.

DETAILED DESCRIPTION OF THE INVENTION AND PREFERRED EMBODIMENTS

Figure 1:
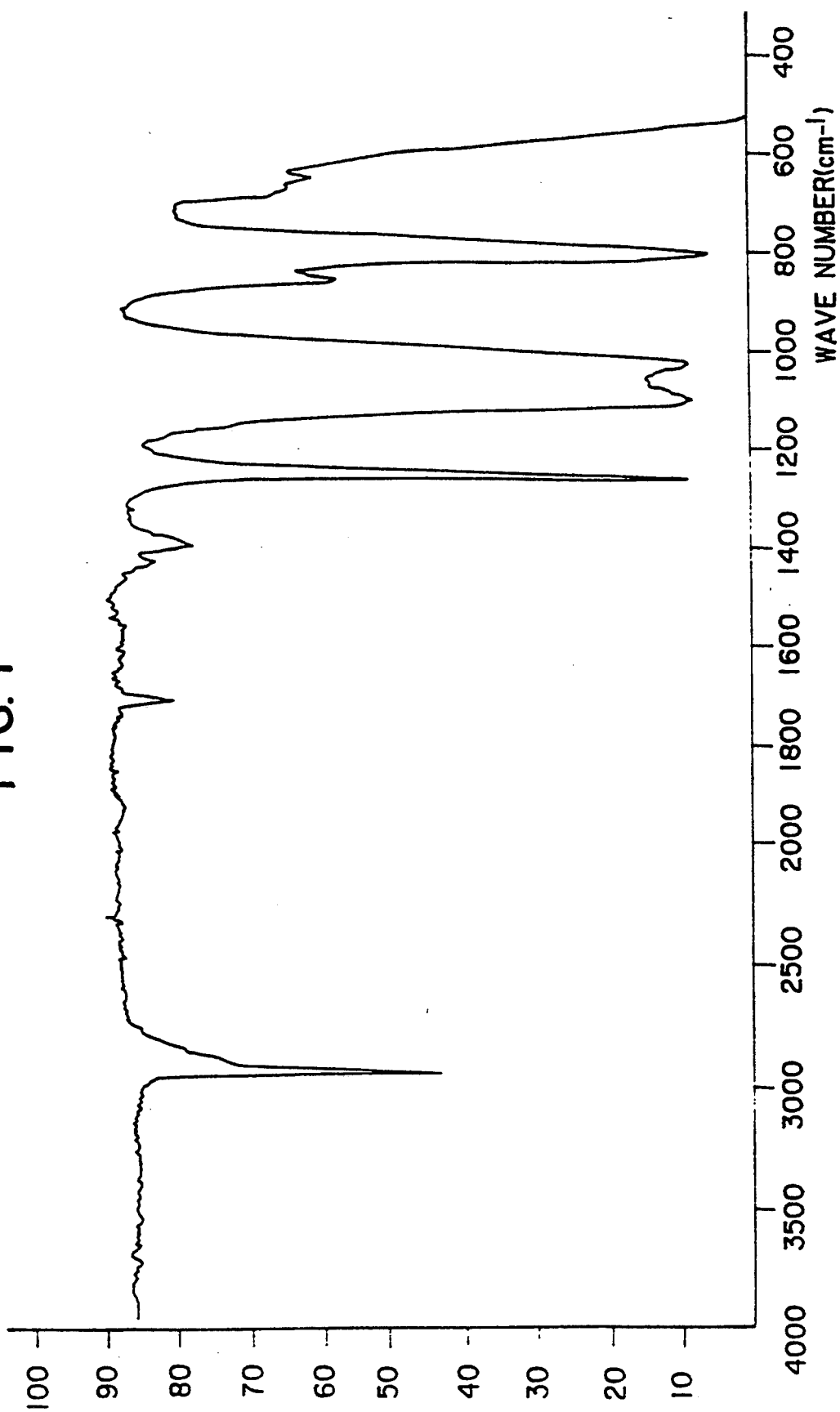
FIG. 1 shows an infrared absorption spectrum of the silicone tetrahydroabietic ester derivative obtained in Example 1.

The silicone esters derivative of formula (I) can be prepared, for example, by whichever process A or B.

Process A:

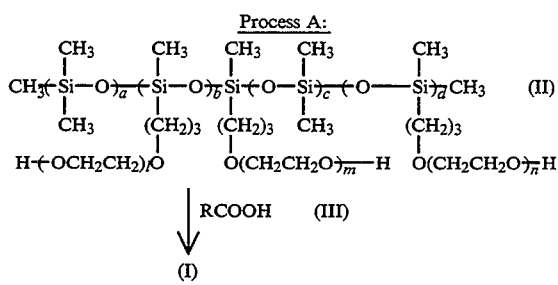

Here, R, a, b, c, 1, m and n have the same meanings as defined before.

In detail, the silicone ester derivative (I) of the present invention can be prepared by the reaction of alcohol-modified silicone (II) with carboxylic acid (III) or its reactive derivative.

The alcohol-modified silicones (i.e., alcohol-modified dimethylpolysiloxane), the starting material of the above process, are commercially available and sold, for example, by Shin'etsu Kagaku Kogyo K. K. They may however be readily synthesized by the reaction of a corresponding polysiloxane having Si—H terminals with an ethylene oxide adduct of allyl alcohol. The molecular weight of alcohol- or allyl alcohol-modified silicones (II) is preferably 130 to 10,000. Moreover, it is preferred that a and b in formula (II) be zero (0) and d be one (1) in view of the availability. They can be used singly or in combination.

Preferable carboxylic acid (III) are saturated or unsaturated, linear, branched or cyclic aliphatic or aromatic carboxylic acids, among which those having 2 to 30 carbon atoms are especially preferred. Examples of the carboxylic acids include acetic acid, butyric acid, capric acid, lauric acid, myristic acid, palmitic acid, stearic acid, behenic acid, melissic acid, palmitoleic acid, oleic acid, linoleic acid, linolenic acid, arachidonic acid, erucic acid, 2-ethylhexanoic acid, 2-hexyldecanoic acid, 2-heptylundecanoic acid, 5,7,7-trimethyl-2-(1,3,3-trimethylbutyl)octanoic acid, methyl branched isostearic acid, cyclopentanecarboxylic acid, cyclohexanecarboxylic acid, abietic acid, dehydroabietic acid, dihydroabietic acid, tetrahydroabietic acid, cholic acid, deoxycholic acid, glycyrrhizic acid, benzoic acid and naphthoic acid. These carboxylic acids (III) may be used singly or in combination. An example of such combination is a mixed hydrogenated abietic acid which is a mixture of dihydroabietic acid and tetrahydroabietic acid.

The mixed hydrogenated abietic acid is a major component of the rosin, and sold, for example, by Harima Kasei Kogyo K.K. This may otherwise be obtained by a catalytic reduction of abetic acid by the use of a metal catalyst such as palladium, platinum and nickel. Moreover, it is readily obtainable from market as a hydrogenated rosin.

Examples of the reactive derivatives of the carboxylic acids (III) include carboxylic acid halides such as carboxylic acid bromide and carboxylic acid chloride.

The esterification between alcohol-modified silicone (II) and carboxylic acid (III) is carried out according to a known method. For instance, (II) and (III) are mixed for dehydrative condensation under moderate heating in the presence of an acidic catalyst such as tin chloride and toluenesulfonic acid, or at a high temperature in the absence of a catalyst. The reaction between alcohol-modified silicone (II) and carboxylic halide is carried out according to a known method, and for instance, it proceeds in the presence of a basic catalyst such as pyridine at room temperature or under heat.

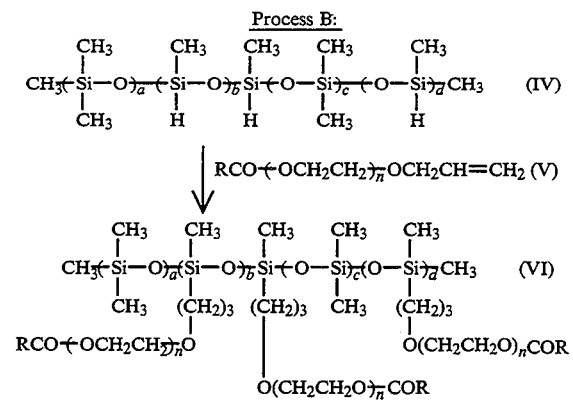

Here, R, a, b, c, d and n have the same meanings as mentioned before.

In detail, polysiloxane (IV) having Si—H bonds and carboxylic acid ester (V) are reacted for hydrosilylation at room temperature or under heat in the presence of a catalytic amount of chloroplantinic acid catalyst. The reaction can be carried out either without solvent or using solvent.

The thus obtained silicone ester derivative (I) of the present invention has features: 1) liquid at room temperature, 2) chemically stable, and 3) very mild to the skin; and is very useful as an oil ingredient for any kind of cosmetic compositions, especially for those which are directly applied to the skin.

The amount of the silicone ester derivative (I) to be incorporated in a cosmetic composition is not particularly limited and generally from 0.001 to 90 wt % of the total composition, with a preferable amount being 0.1 to 80 wt % and most preferably 1 to 50 wt %.

When a polyol-type moisturizer is used in combination with the silicone ester derivative (I), moisturizing effect as well as thick and moistened feel are obtained with a reduced stickiness compared to when the respective ingredients are used singly. Examples of the polyol-type moisturizer include propylene glycol, 1,3-butanediol, dipropylene glycol, glycerol, diglycerol, polyglycerol, tritirol propane, erythritol, pentaerythritol, sorbitane, glucose, sorbitol, martitol, saccharose, trehalose, polyoxyethylene methyl glucoside, polyoxypropylene methyl glucoside and polyethylene glycol. Among them, especially preferred are 1,3-butanediol, glycerol, sorbitol and polyoxyethylene methyl glucoside. These polyol-type moisturizers are preferably incorporated in a cosmetic composition from 2 to 90 wt % and more preferably from 5 to 50 wt % based on the total amount. If the amount is less than 2 wt %, advantage of the combination use is not notable, while at an amount exceeding 90 wt %, the moisture-retaining effect is saturated and no further effect will be observed. The blending proportion between the silicone ester derivative (I) and the polyol-type moisturizer is arbitrary.

Aside from the above-indicated ingredients, the cosmetic compositions according to the present invention may further contain, so far as the effects of the invention are not impeded, oils, surfactants, moisturizers, UV absorbers, chelating agents, pH adjusters, preservatives, viscosity colorants, and perfumes which are generally used in the art.

There is no specific restrictions as to the category of the cosmetic compositions or their forms. Examples of the cosmetic compositions include skin-care compositions such as W/O- and O/W-emulsified cosmetic products, creams, lotions and milky lotions, oil-base cosmetic compositions, lipsticks, foundations, skin detergents, hair tonics, hair setting agents, hair growers, hair nourishing agents and so on.

The silicone ester derivative (I) of the present invention is applicable to a variety of blending systems in the art. This may be explained by the fact that there are three different parts in a molecule of the ester derivative (I), which are dimethylpolysiloxisane part, carboxylic hydrophobic part and ester or ethylene dioxy group part, and these three parts are capable of undergoing interaction with silicone oil, hydrocarbon oil and polar solvent or water, respectively.

Thus, when the silicone ester derivative (I) of the present invention is incorporated into any compositions such as cosmetic or skin-care compositions which are comprised of a hydrocarbon oil, a polar solvent, water and so on, it is capable of maintaining the compositions stable for a prolonged period. Moreover, due to the presence of the ester derivative (I), the cosmetic compositions according to this invention remarkably reduce creaky feel on use which the conventional silicone oils couldn't avoid. Especially, it is notable that when silicone ester derivative (I) and a polyol-type moisturizer are used in combination for preparing a cosmetic composition, excellent properties are obtainable which include enhanced moisture-retainability and thick and moistened feel with supressed stickiness.

EXAMPLES

This invention will now be explained by way of Examples, which should not be construed as limiting the invention thereto.

EXAMPLE 1

Tetrahydroabietic Ester Derivative of Alcohol-modified Silicone

In a 200 ml two-necked flask equipped with a stirrer, dropping funnel and a reflux condenser was placed a 30 g (5.35 mmol) of alcohol-modified silicone (product of Shin'etsu Kagaku Kogyo K. K.; a+b=0, c(mean value)=72, d=1, m+n=3 in formula (II)), 0.93 g (11.7 mmol) of pyridine and 60 g of toluene. The flask was stirred under nitrogen atmosphere at room temperature. 10 ml of toluene containing 3.80 g (11.7 mmol) of tetrahydroabietoyl chloride was dropped into the flask over 20 minutes. After the completion of the dropping, the flask was heated at 80° C. and subjected to 15 hours consecutive stirring under heat. Thereafter, the flask was allowed to stand for cooling down and 3 ml methanol was added to decompose the remaining tetrahydroabietoyl chloride. The toluene layer was washed four times with 50 ml water. After the solvent was evaporated, the obtained yellow viscous product was subjected to silica gel column chromatography (silica gel: 230-400 mesh, solvents: dichloromethane/hexane=1-4/1, dichloromethane only) to obtain 25.6 g of the title compound as a pale-yellow viscous material

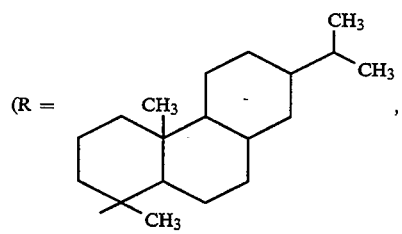

a+b=0, c̄ (mean value)=72, d=1, m+n=3 in formula (I)).

Yield: 77.5%

IR(liquid film, cm$^{-1}$): 2964, 1732, 1446, 1416, 1262, 1096, 1024, 868, 802, 662 (FIG. 1)

Figure 2:
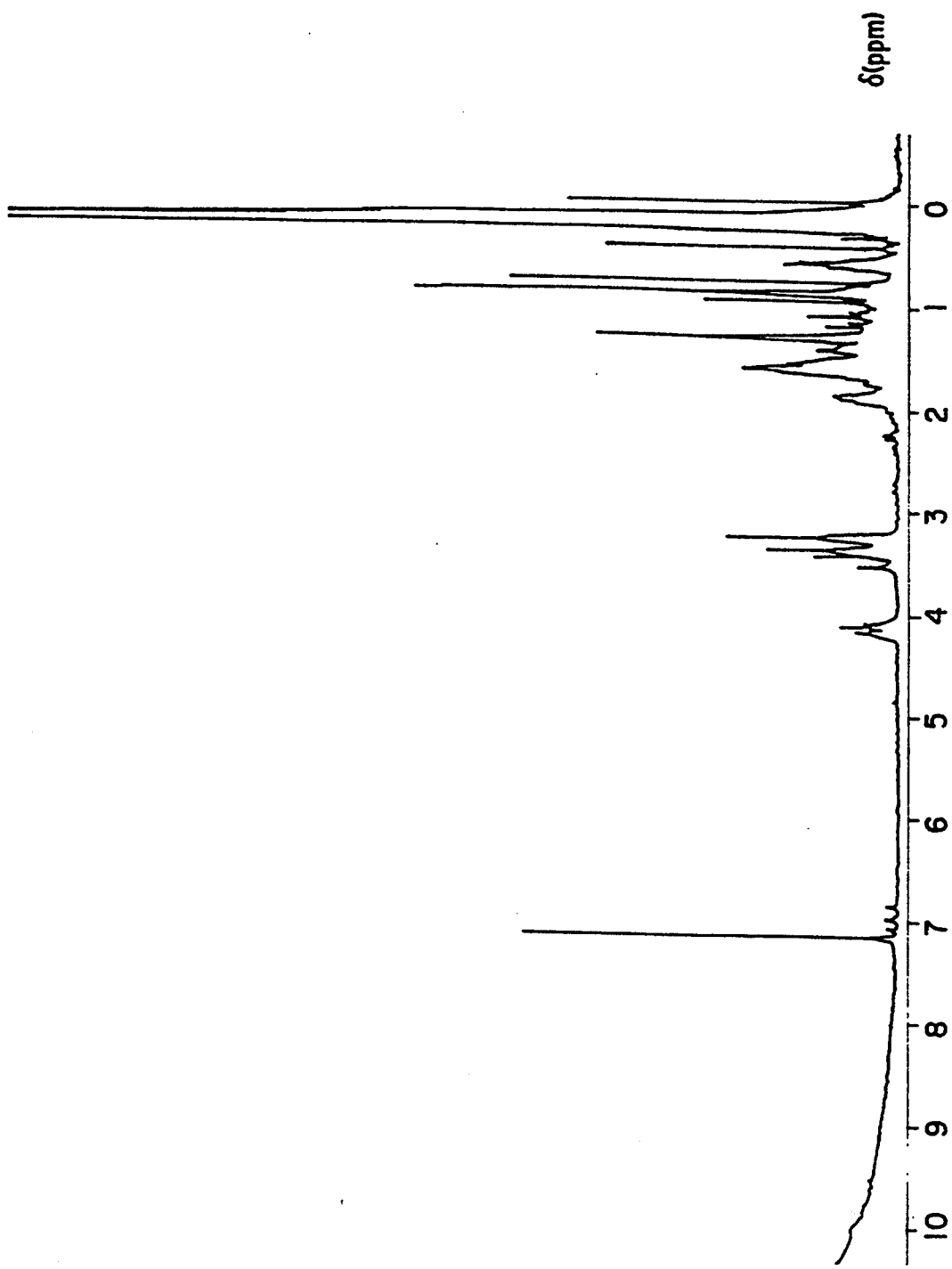
FIG. 2 shows a $^1$H-NMR spectrum of the silicone tetrahydroabietic ester derivative obtained in Example 1.

$^1$H-NMR (C$_6$D$_6$, δ) 0.1~0.3 (C$\underline{H}_3$—Si about 450 H) 0.5~2.0 (H derived from tetrahydroabietic acid, Si—C$\underline{H}_2$—C$\underline{H}_2$—C$\underline{H}_2$—O, 76 H) 3.2~3.5 (Si—CH$_2$C$\underline{H}_2$—C$\underline{H}_2$—O—C$\underline{H}_2$—CH$_2$—O—C$\underline{H}_2$—, 12 H) 4.0~4.3 (CO$_2$—C$\underline{H}_2$—, 4 H) (FIG. 2)

Figure 3:
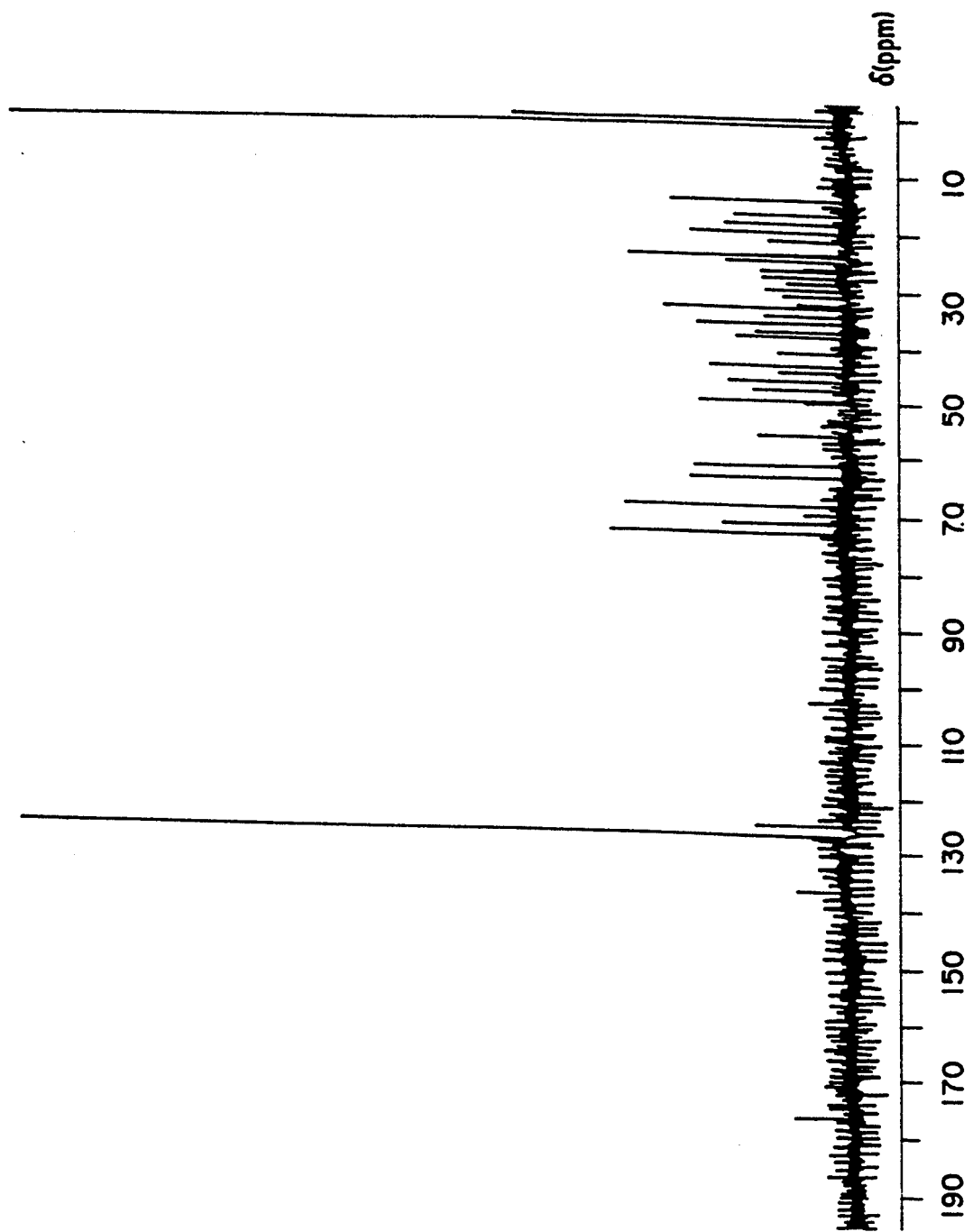
FIG. 3 shows a $^{13}$C-NMR spectrum of the silicone tetrahydroabietic ester derivative obtained in Example 1.
Figure 4:
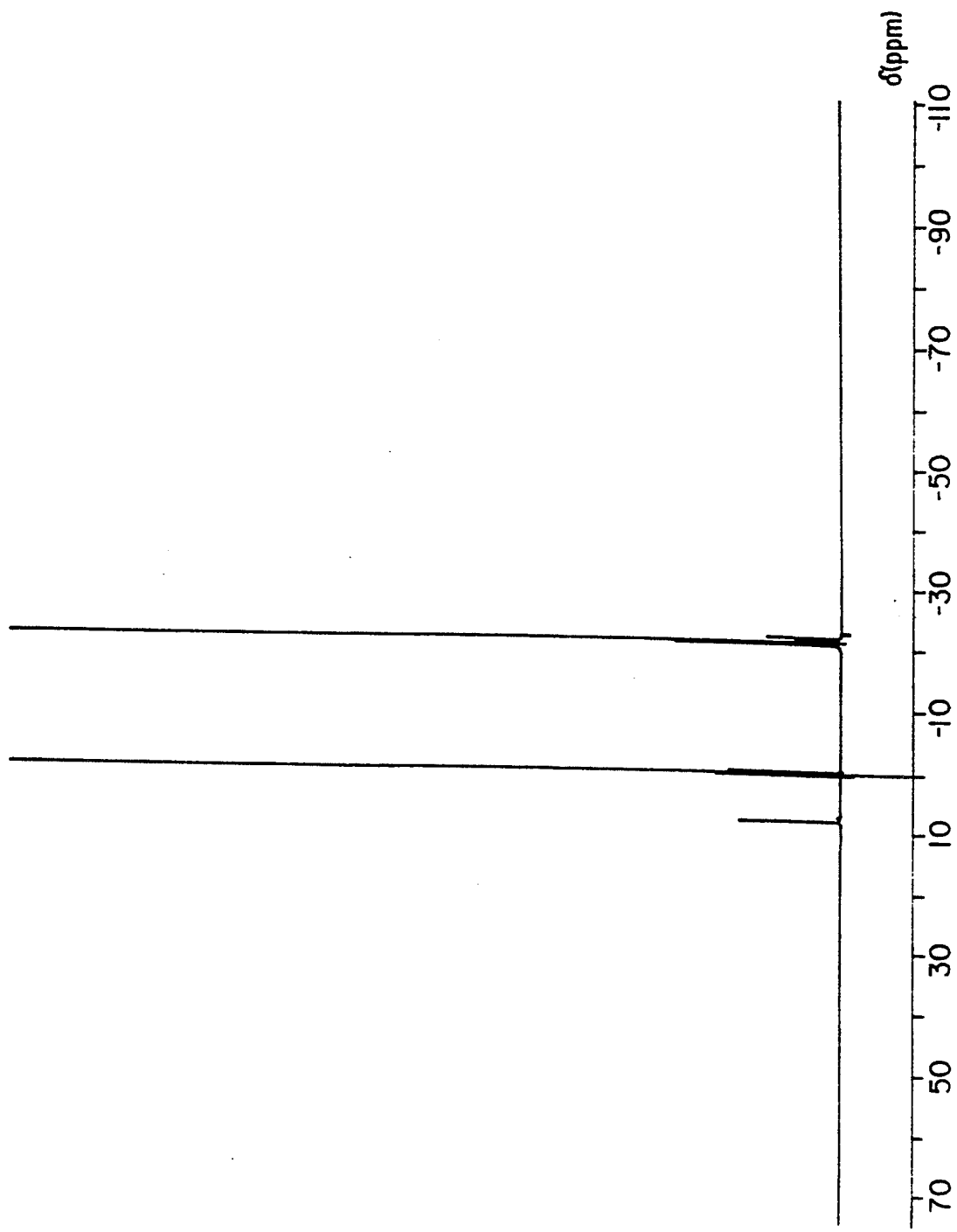
FIG. 4 shows a $^{29}$Si-NMR spectrum of the silicone tetrahydroabietic ester derivative obtained in Example 1.

$^{13}$C-NMR (C$_6$D$_6$, δ) 0.3~1.9 (C$\underline{H}_3$—Si, C$\underline{H}_2$—Si) 14.6~56.2 (C$\underline{H}_3$ derived from tetrahydroabietic acid, C$\underline{H}_2$, C$\underline{H}$, SiCH$_2$—C$\underline{H}_2$—CH$_2$—O) 61.9, 63.7 (SiCH$_2$C$\underline{H}_2$CH$_2$—O) 69.0 (—C$\underline{H}_2$OCH$_2$C$\underline{H}_2$OCH$_2$—) 72.2, 74.0 (—C$\underline{H}_2$OCO—) 178.0 (—C$\underline{O}$O—) (FIG. 3)

$^{29}$Si-NMR(C$_6$D$_6$, δ)

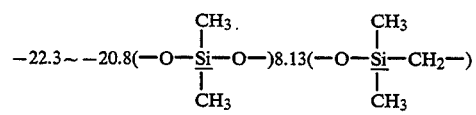

(FIG. 4)

EXAMPLE 2

Tetrahydroabietic Ester Derivative of Alcohol-modified Silicone

The process of Example 1 was followed using 30 g (30 mmol) of alcohol-modified silicone (product of Shin'etsu Kagaku Kogyo K. K.; a+b=0, c̄ (mean value)=10, d=1, m=n=1 in formula (II)), 10.44 g (132 mmol) of pyridine, 60 g of toluene and 23.39 g (72 mmol) of tetrahydroabietoyl chloride to obtain 33.1 g of the title compound as a pale-yellow, viscous material

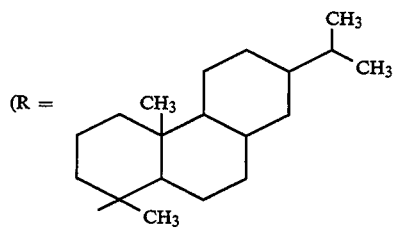

a+b=0, c̄ (mean value)=10, d=1, m=n=1 in formula (I)).

Yield: 69.9%

Figure 5:
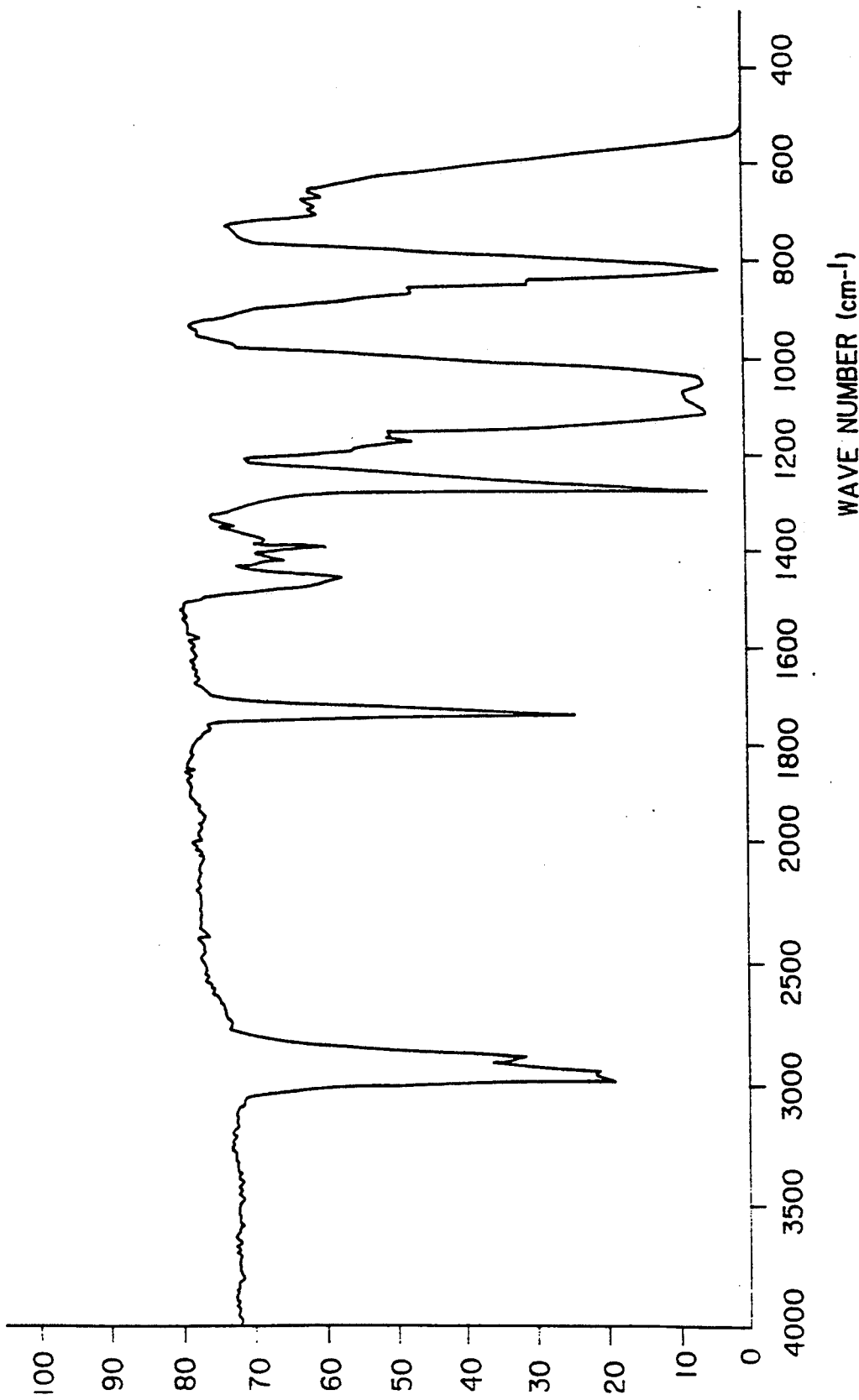
FIG. 5 shows an infrared absorption spectrum of the silicone tetrahydroabietic ester derivative obtained in Example 2.

IR(liquid film, cm$^{-1}$) 2962, 2872, 1731, 1455, 1416, 1389, 1371, 1260, 1170, 1095, 1038, 801, 702, 687, 666 (FIG. 5)

Figure 6:
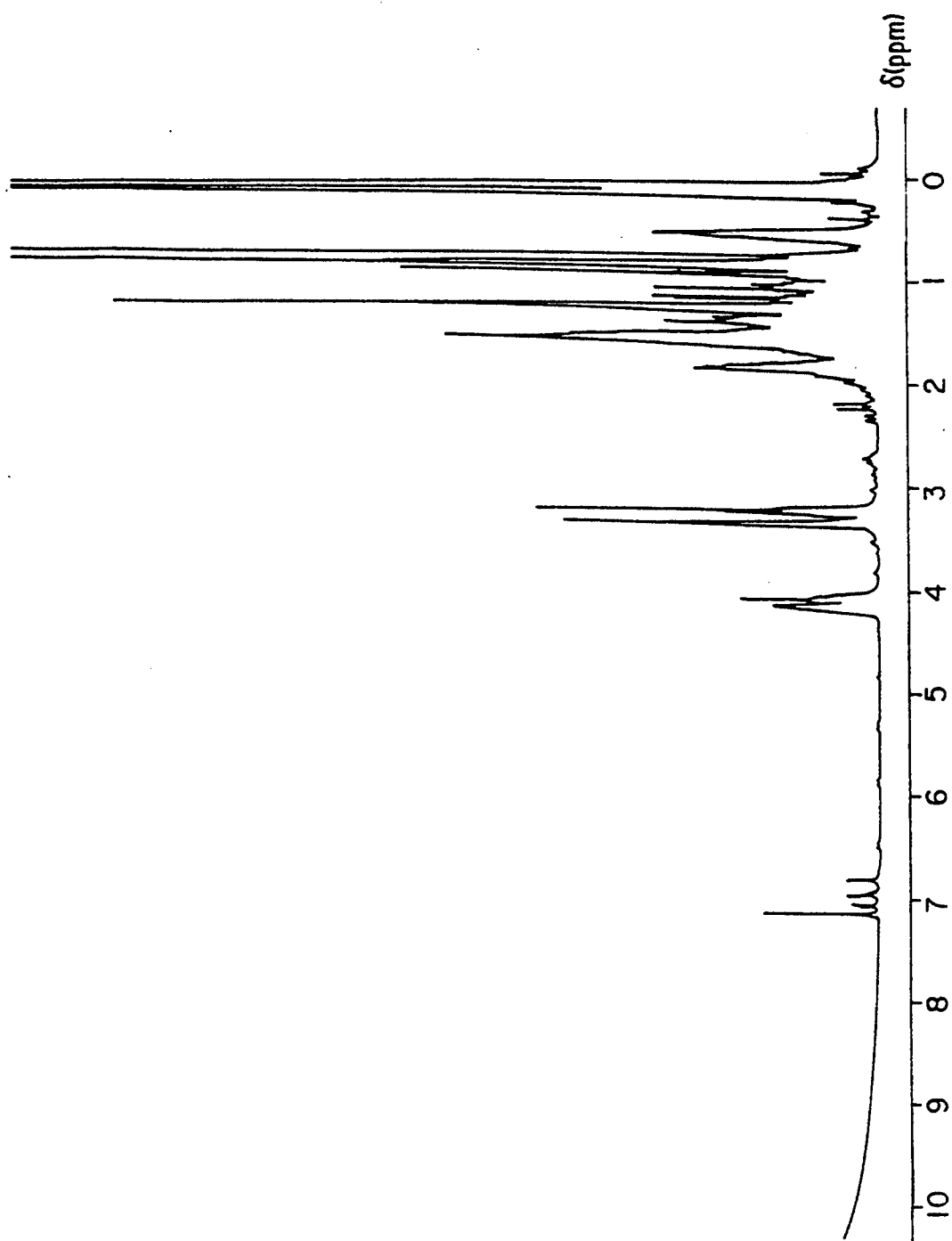
FIG. 6 shows a $^1$H-NMR spectrum of the silicone tetrahydroabietic ester derivative obtained in Example 2.

$^1$H-NMR (C$_6$D$_6$, δ) 0.1~0.3 (C$\underline{H}_3$—Si about 72 H) 0.5~2.0 (H derived from tetrahydroabietic acid, Si—C$\underline{H}_2$—C$\underline{H}_2$—C$\underline{H}_2$—O, 76 H) 3.24, 3.37 (SiCH$_2$C$\underline{H}_2$—C$\underline{H}_2$—O—C$\underline{H}_2$—, 4 H each) 4.0~4.2 (—C$\underline{H}_2$OCO—, 4 H) (FIG. 6)

Figure 7:
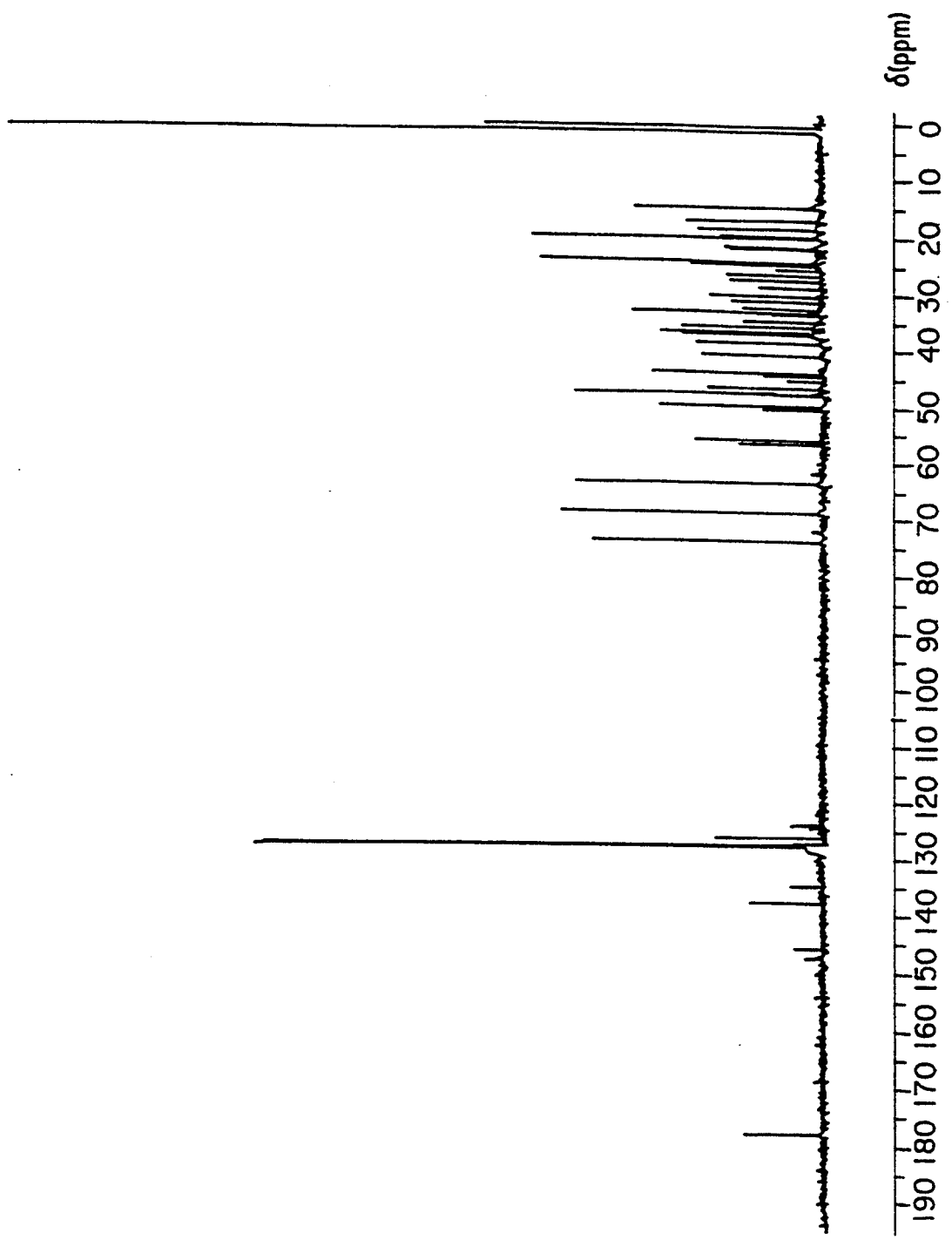
FIG. 7 shows a $^{13}$C-NMR spectrum of the silicone tetrahydroabietic ester derivative obtained in Example 2.
Figure 8:
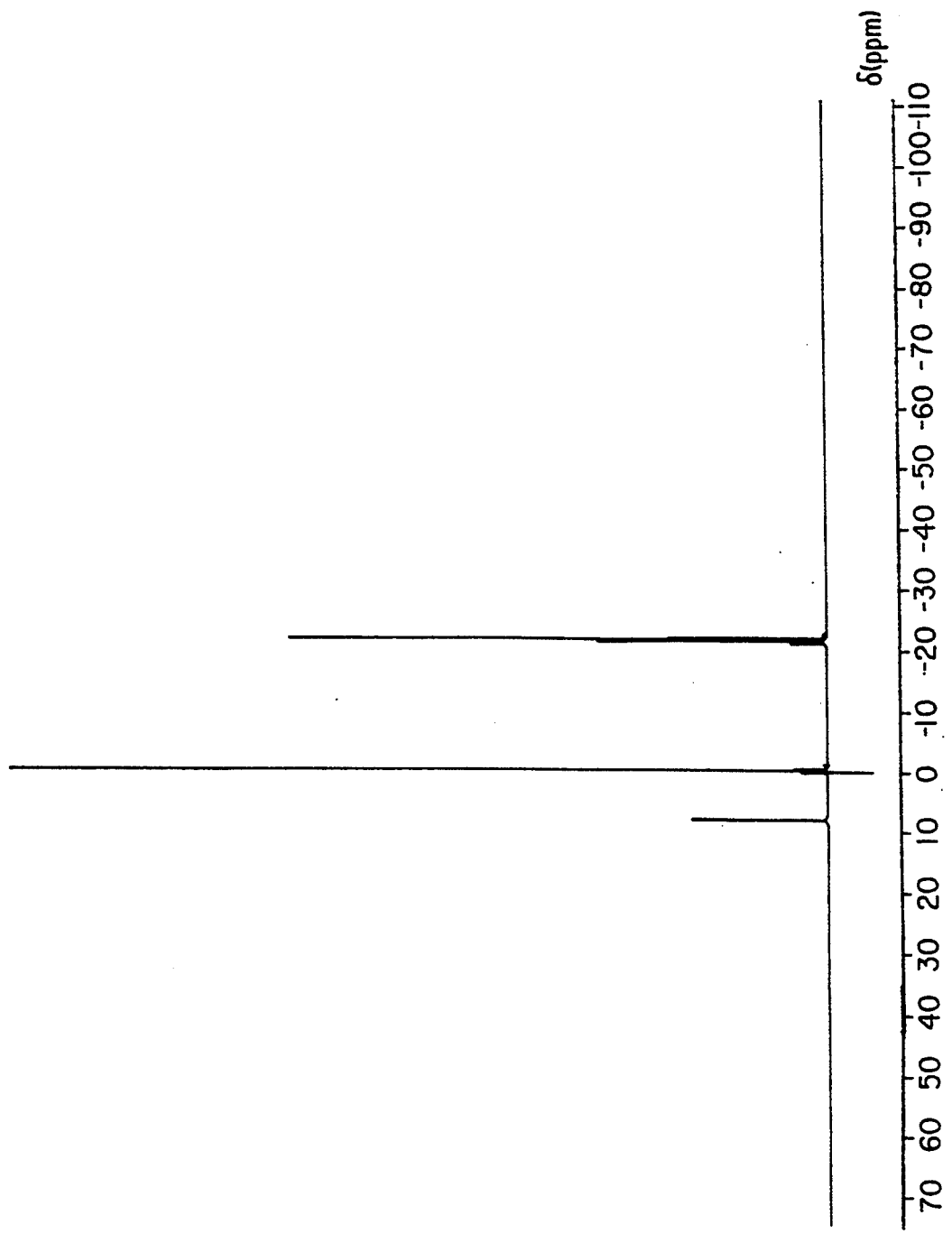
FIG. 8 shows a $^{29}$Si-NMR spectrum of the silicone tetrahydroabietic ester derivative obtained in Example 2.

$^{13}$C-NMR (C$_6$D$_6$, δ) 0.3~1.5 (CH$_3$—Si, CH$_2$—Si) 14.6~56.9 (CH$_3$ derived from tetrahydroabietic acid, CH$_2$, CH, Si—CH$_2$—CH$_2$—CH$_2$—O) 63.6 (SiCH$_2$CH$_2$—CH$_2$—O) 69.0 (SiCH$_2$CH$_2$CH$_2$CH$_2$O—CH$_2$—CH$_2$) 73.9 (—CH$_2$OCO—) 178.0 (—COO—) (FIG. 7)

$^{29}$Si-NMR (C$_6$D$_6$, δ)

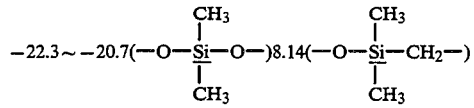

(FIG. 8)

EXAMPLES 3-10

The process of Example 1 was followed to obtain silicone ester derivatives (I) tabulated in Table 1.

TABLE 1

| Example Nos. | RCO— | a + b | c (mean value) | d | l | m + n |
|---|---|---|---|---|---|---|
| Ex. 3 | Tetrahydroabietic acid residue | 0 | 50 | 1 | 0 | 3 |
| Ex. 4 | Dehydroabietic acid residue | 0 | 12 | 1 | 0 | 2 |
| Ex. 5 | Dehydroabietic acid residue | 0 | 21 | 1 | 0 | 2 |
| Ex. 6 | Isostearic acid residue | 0 | 25 | 1 | 0 | 3 |
| Ex. 7 | Cholic acid residue | 0 | 50 | 1 | 0 | 2 |
| Ex. 8 | Abietic acid residue | 0 | 70 | 1 | 0 | 4 |
| Ex. 9 | Oleic acid residue | 0 | 14 | 1 | 0 | 2 |
| Ex. 10 | Dihydroabietic acid residue | 0 | 25 | 1 | 0 | 2 |

EXAMPLE 11

Synthesis of Tetrahydroabietic Ester Derivative of Alcohol-modified Silicone (RCO=tetrahydroabietic acid residue, a=b=0, c (mean value)=14, d=1 in formula (VI))

In a 30 ml round bottomed flask, 14.04 g (12.0 mmol) of siloxane oligomer (product of Toshiba Silicone K.K.; a=b=0, c=14, d=1), 7.00 g (20.2 mmol) of allyl tetrahydroabietate and a catalyst amount of chloroplatinic acid.6H$_2$O were placed and mixed. After stirring over 24 hours at room temperature, 100 ml of hexane was added, and the hexane layer was washed three times with 50 ml water. The hexane layer was dried over sodium sulfate and the solvent was evaporated. A dark brown oily material was obtained. This material was purified through medium-pressure liquid chromatography (Silica gel 25~40 μm 350 g; hexane/ethyl acetate=29/1) to obtain 14.74 g of the title compound as a pale-yellow oily material. Yield: 77.7%

Figure 9:
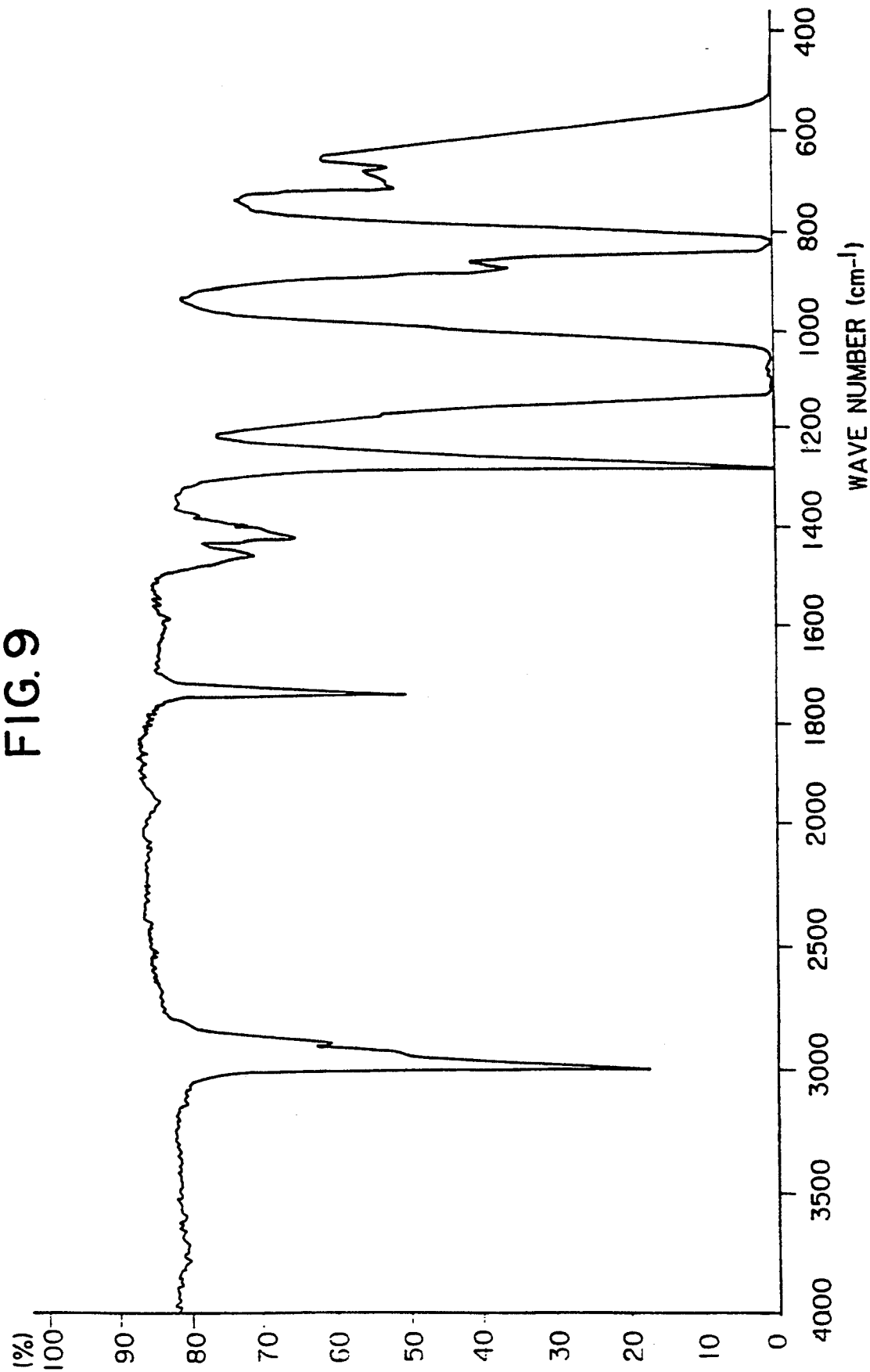
FIG. 9 shows an infrared absorption spectrum of the silicone tetrahydroabietic ester derivative obtained in Example 11.

IR(liquid film, cm$^{-1}$) 2964, 2872, 1730, 1580, 1540, 1450, 1414, 1388, 1262, 1104, 1032, 864, 810, 702, 664 (FIG. 9)

Figure 10:
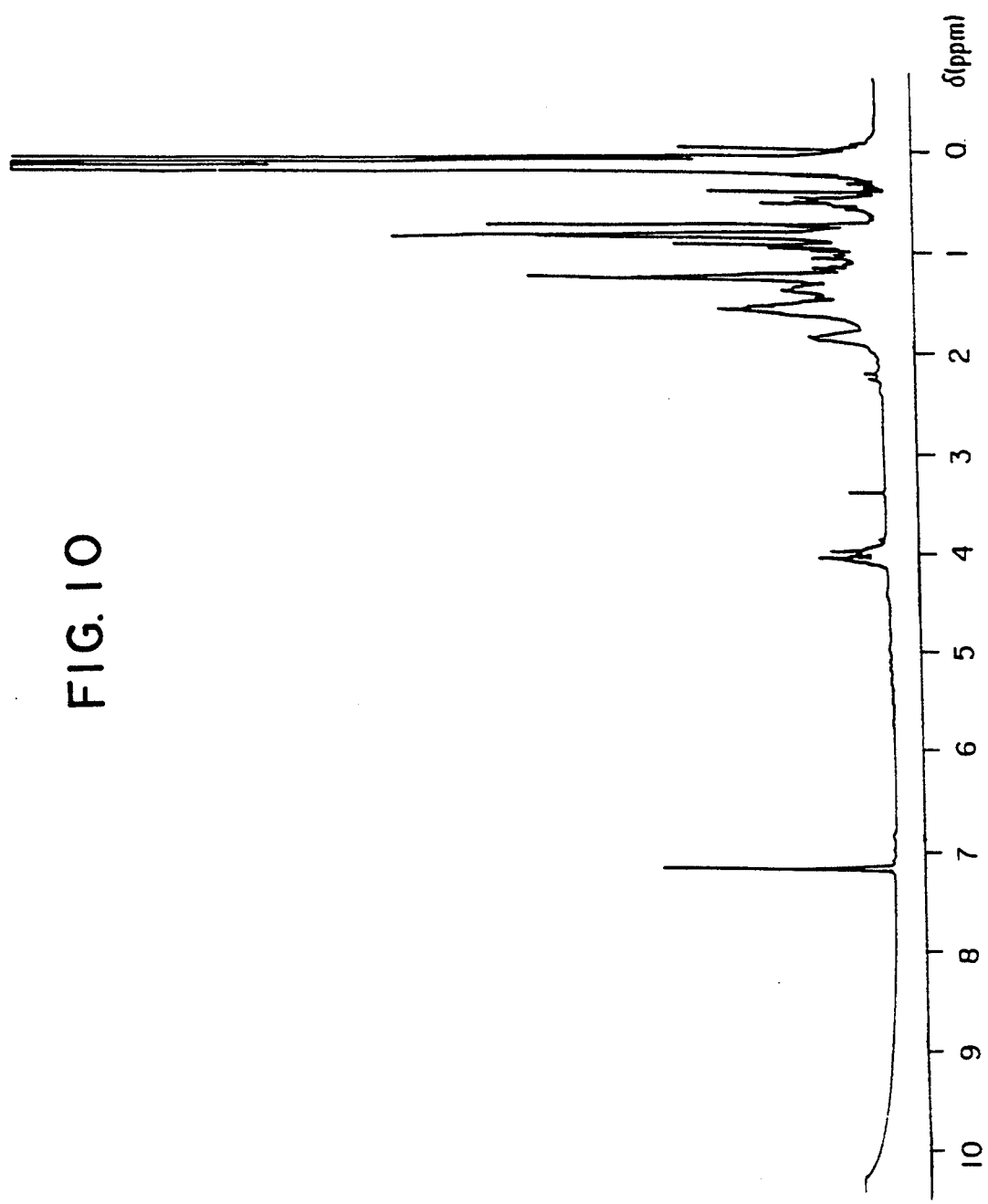
FIG. 10 shows a $^1$H-NMR spectrum of the silicone tetrahydroabietic ester derivative obtained in Example 11.

$^1$H-NMR(C$_6$D$_6$, δ) 0.1–0.3 (CH$_3$—Si, about 96 H) 0.5–2.0 (H derived from tetrahydroabietic acid, Si—CH$_2$—CH$_2$—CH$_2$—O, 74 H), 4.01 (—CH$_2$—O$_2$C—, 4 H) (FIG. 10)

Figure 11:
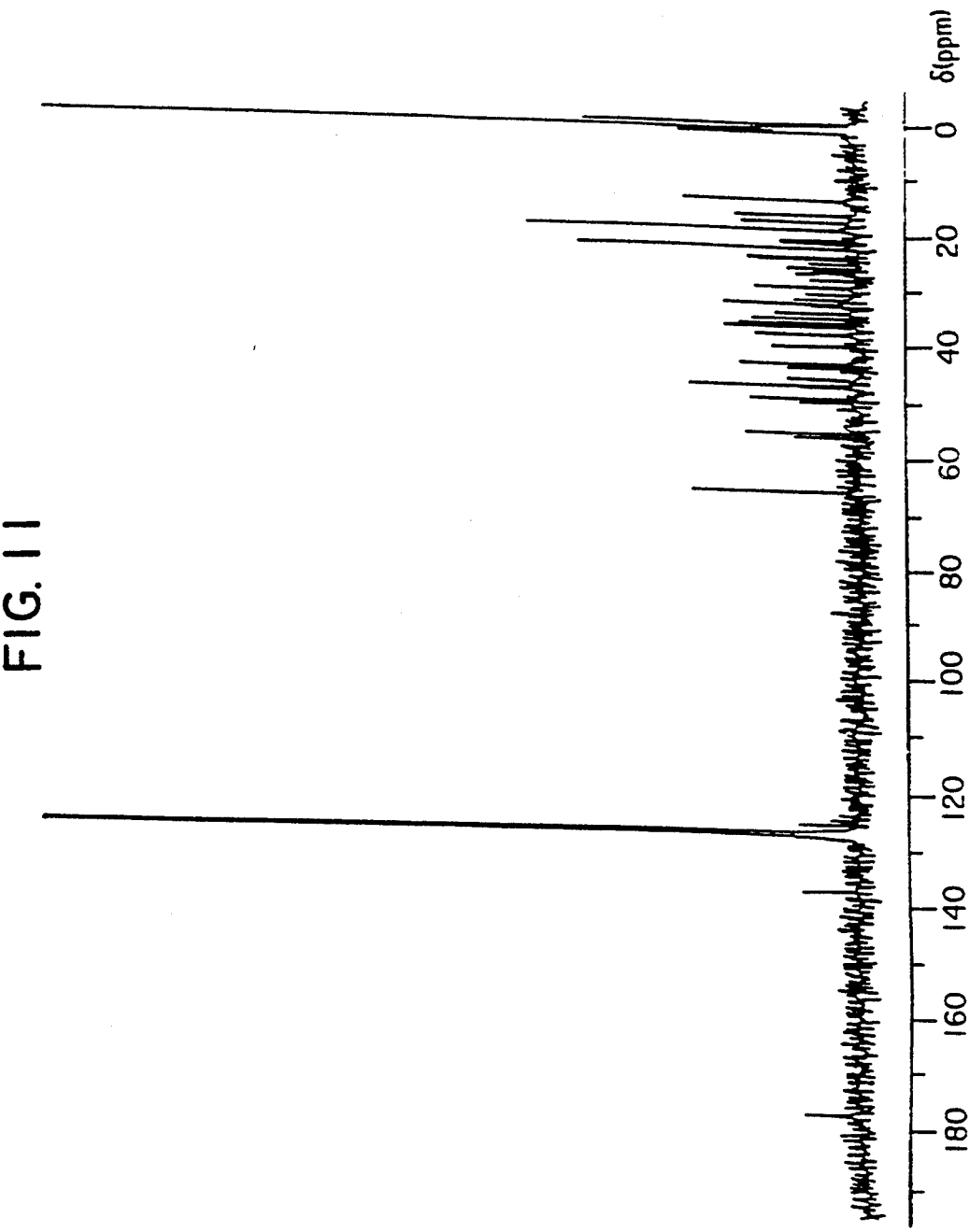
FIG. 11 shows a $^{13}$C-NMR spectrum of the silicone tetrahydroabietic ester derivative obtained in Example 11.
Figure 12:
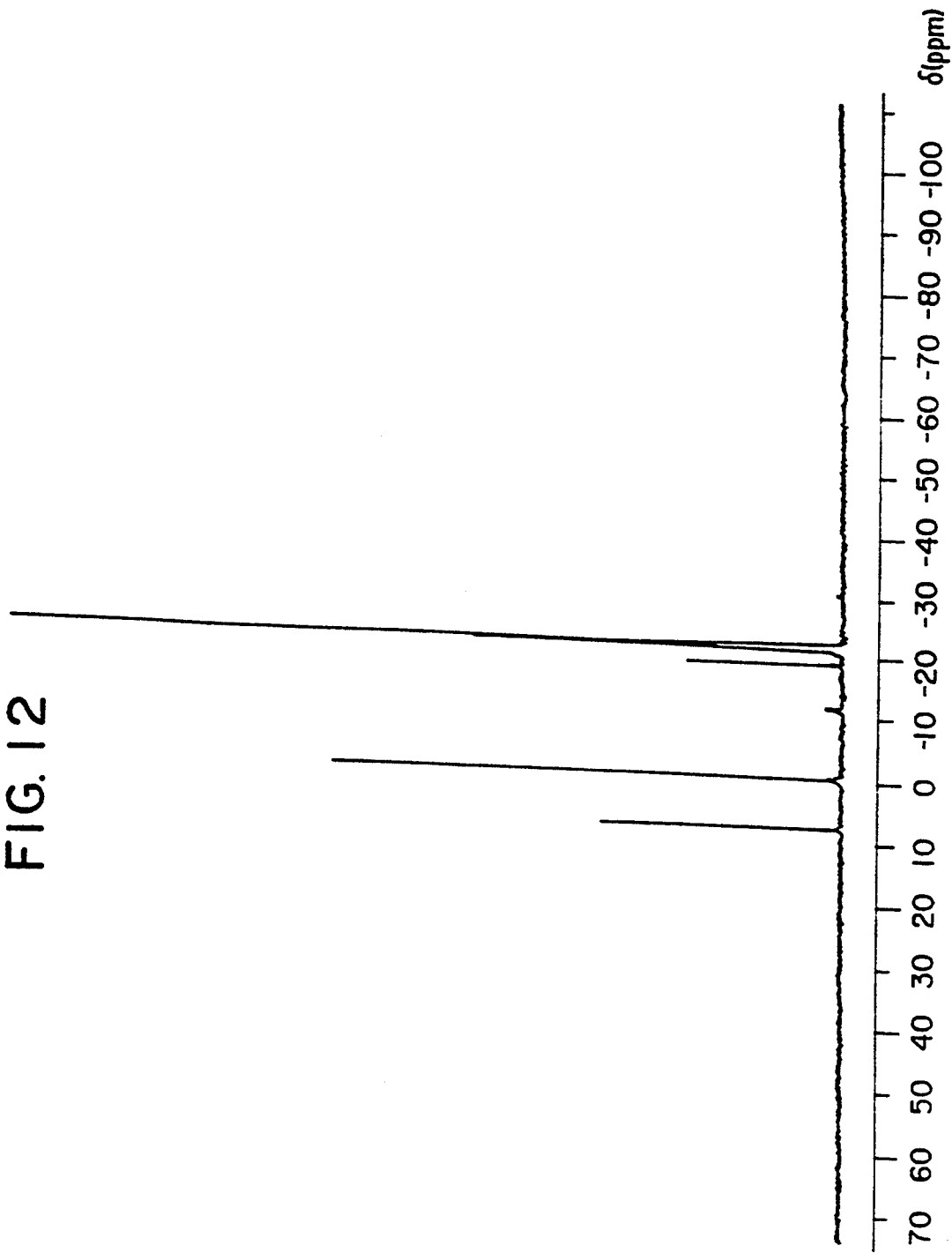
FIG. 12 shows a $^{29}$Si-NMR spectrum of the silicone tetrahydroabietic ester derivative obtained in Example 11.

$^{13}$C-NMR(C$_6$D$_6$, δ) 0.3–1.5 (CH$_3$—Si, CH$_2$—Si), 14.5–57.0 (CH$_3$ derived from tetrahydroabietic acid, CH$_2$, CH, Si—CH$_2$—CH$_2$—CH$_2$), 66.9 (—CH$_2$—O$_2$C—), 178.0 (—COO—) (FIG. 11)

$^{29}$Si-NMR(C$_6$D$_6$, δ)

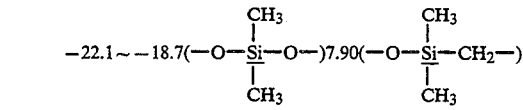

(FIG. 12)

EXAMPLES 12-24

The process of Example 11 was followed to obtain silicone ester derivatives (I) tabulated in Table 2.

TABLE 2

| Example Nos. | RCO— | a b c d | l | m | n |
|---|---|---|---|---|---|
| Ex. 12 | Tetrahydroabietic acid residue | a + c = 40, b = 4, d = 0 | 0 | 0 | 0 |
| Ex. 13 | Dihydroabietic acid residue | a = b = 0, c = 22, d = 1 | 0 | 0 | 0 |
| Ex. 14 | Dihydroabietic acid residue | a + c = 14, b = 2, d = 0 | 0 | 0 | 0 |
| Ex. 15 | Dihydroabietic acid residue | a + c = 80, b = 20, d = 0 | 0 | 0 | 0 |
| Ex. 16 | Tetrahydroabietic acid residue | a + c = 42, b = 10, d = 0 | 0 | 0 | 0 |
| Ex. 17 | Tetrahydroabietic acid residue | a + c = 14, b = 3, d = 0 | 0 | 0 | 0 |
| Ex. 18 | Dihydroabietic acid residue | a + c = 22, b = 10, d = 0 | 0 | 0 | 0 |
| Ex. 19 | Tetrahydroabietic acid residue | a = b = 0, c = 50, d = 1 | 0 | 0 | 0 |
| Ex. 20 | Tetrahydroabietic acid residue | a = b = 0, c = 72, d = 1 | 0 | 0 | 0 |
| Ex. 21 | Tetrahydroabietic acid residue | a + c = 60, b = 5, d = 0 | 0 | 0 | 0 |
| Ex. 22 | Tetrahydroabietic acid residue | a + c = 12, b = 4, d = 0 | 0 | 0 | 0 |
| Ex. 23 | Tetrahydroabietic acid residue | a + c = 12, b = 8, d = 0 | 0 | 0 | 0 |
| Ex. 24 | Dihydroabietic acid residue | a + c = 36, b = 8, d = 0 | 0 | 0 | 0 |

*All values are mean values.

EXAMPLE 25

Emulsified Cosmetic Composition

Emulsified cosmetic compositions shown in Table 3 were prepared according to the process below. Evaluation was made by ten (10) expert panelists, which results are also shown in Table 3.

Process

Ingredients 1) to 4) in Table 3 were mixed under heat, to which a mixture of 5) and 6) were added and stirred to obtain a substantially homogeneous solution. Comparative products were prepared by the same manner.

TABLE 3

| | Emulsified cosmetic composition | Invention Product 1 | Invention Product 2 | Comparative Product 1 | Comparative Product 2 | Comparative Product 3 |
|---|---|---|---|---|---|---|
| Composition (%) | 1) Silicone ester derivative (I) (Example 3; R = tetrahydroabietic acid residue, a + b = 0, c = 50, d = 1, m + n = 3, l = 0) | 10.0 | — | — | 10.0 | — |
| | 2) Silicone ester derivative (I) (Example 1; R = tetrahydroabietic acid residue, | — | 10.0 | — | — | 10.0 |

TABLE 3-continued

| Emulsified cosmetic composition | | Invention Product 1 | Invention Product 2 | Comparative Product 1 | Comparative Product 2 | Comparative Product 3 |
| --- | --- | --- | --- | --- | --- | --- |
| | $a + b = 0, c = 72, d = 1, m + n = 3, 1 = 0$) | | | | | |
| | 3) Squalane | — | — | 10.0 | — | — |
| | 4) Polyoxyethylene oleylether (20 E.O.) | 2.0 | 2.0 | 2.0 | 2.0 | 2.0 |
| | 5) Glycerol | 8.0 | 8.0 | 8.0 | — | — |
| | 6) Purified Water | Balance | Balance | Balance | Balance | Balance |
| Feel on Use | Moistness | Yes (moistened) | Yes | Yes | No | No |
| | Stickiness | slightly unsticky | slightly unsticky | Yes (sticky) | No | No |
| | Smoothness | Yes (smooth) | Yes | No | Yes | Yes |
| | Effectiveness for chapped skin | Yes (effective) | Yes | Yes | slightly uneffective | slightly uneffective |

EXAMPLE 26

Moisturizing Cream

Moisturizing creams formulated as shown in Table 4 were prepared according to the process below. Evaluation was made by ten(10) expert panelists, which results are also shown in Table 4.

Process

Ingredients 1) to 8) and 11) to 13) in Table 4 were allowed to dissolve under heat, and the temperature was maintained at 70° C. Ingredients 9), 10) and 15) were also mixed at 70° C., to which the mixture of 1) to 8) and 11) to 13) was added. The obtained mixture was charged in an emulsifier for emulsification. The resultant emulsion was added with ingredient 14) and cooled down to 30° C. by a heat exchanger to obtain a moisturizing cream.

TABLE 4

| | Moisturizing cream | Invention Product 3 | Invention Product 4 | Comparative Product 4 |
| --- | --- | --- | --- | --- |
| Composition (%) | 1) Silicone ester derivative (I) (Ex. 4, R = dehydroabietic acid residue, $a + b = 0, c = 12, d = 1, m + n = 2, 1 = 0$) | 8.0 | — | — |
| | 2) Silicone ester derivative (I) (Ex. 5, R = dehydroabietic acid residue, $a + b = 0, c = 21, d = 1, m + n = 2, 1 = 0$) | — | 8.0 | — |
| | 3) Liquid paraffin | — | — | 8.0 |
| | 4) Bees wax | 2.0 | 2.0 | 2.0 |
| | 5) Stearyl alcohol | 3.0 | 3.0 | 3.0 |
| | 6) Stearic acid | 5.0 | 5.0 | 5.0 |
| | 7) Squalane | 7.0 | 7.0 | 7.0 |
| | 8) Polyoxyethylene oetylether (20 E.O.) | 1.0 | 1.0 | 1.0 |
| | 9) Propylene glycol | 8.0 | 8.0 | 8.0 |
| | 10) Glycerol | 4.0 | 4.0 | 4.0 |
| | 11) Triethanolamine | 1.0 | 1.0 | 1.0 |
| | 12) Methyl paraben | 0.1 | 0.1 | 0.1 |
| | 13) Butyl paraben | 0.1 | 0.1 | 0.1 |
| | 14) Perfume | 0.1 | 0.1 | 0.1 |
| | 15) Purified water | Balance | Balance | Balance |
| Feel on Use | Moistness | Yes (moistened) | Yes | slightly (moistened) |
| | Stickiness | No | No | Yes (sticky) |
| | Smoothness | Yes (smooth) | Yes | No |
| | Effectiveness for chapped skin | Yes (effective) | Yes | slightly (effective) |

EXAMPLE 27

Emulsified Cosmetic Composition

Emulsified cosmetic compositions shown in Table 5 were prepared according to the process below. Evaluation was made by the(10) expert panelists, which results are also shown in Table 5.

Process

Ingredients 1) to 4) in Table 5 were mixed under heat and added with a mixture of 5) and 6) to obtain a substantially homogeneous solution by stirring. Comparative products were prepared by the same manner.

TABLE 5

| | Emulsified cosmetic composition | Invention Product 5 | Invention Product 6 | Comparative Product 5 | Comparative Product 6 | Comparative Product 7 |
| --- | --- | --- | --- | --- | --- | --- |
| Composition (%) | 1) Silicone ester derivative (I) (Ex. 11) | 10.0 | — | — | 10.0 | — |
| | 2) Silicone ester derivative (I) (Ex. 12) | — | 10.0 | — | — | 10.0 |
| | 3) Liquid paraffin | — | — | 10.0 | — | — |
| | 4) Polyoxyethylene oleyl ether (20 E.O.) | 2.0 | 2.0 | 2.0 | 2.0 | 2.0 |
| | 5) Glycerol | 8.0 | 8.0 | 8.0 | — | — |
| | 6) Purified water | Balance | Balance | Balance | Balance | Balance |
| Feel on Use | Moistness | Yes (moistened) | Yes | Yes | No | No |

TABLE 5-continued

| Emulsified cosmetic composition | Invention Product 5 | Invention Product 6 | Comparative Product 5 | Comparative Product 6 | Comparative Product 7 |
| --- | --- | --- | --- | --- | --- |
| Stickiness | slightly unsticky | slightly unsticky | Yes (sticky) | No | No |
| Smoothness | Yes (smooth) | Yes | No | Yes | Yes |
| Effectiveness for chapped skin | Yes (effective) | Yes | Yes | slightly uneffective | slightly uneffective |

EXAMPLE 28

Moisturizing Cream

Moisturizing creams formulated as shown in Table 6 were prepared according to the process below. Evaluation was made by ten(10) panelists, which results are also shown in Table 6.

Process

Ingredients 1) to 8) and 11) to 13) in Table 6 were allowed to dissolve under heat, and the temperature was maintained at 70° C. In the same manner, ingredients 9), 10) and 15) were heated and mixed, to which the mixture of 1) to 8) and 11) to 13) was added. The obtained mixture was charged in an emulsifier for emulsification. Ingredient 14) was added to the resultant emulsion and cooled down to 30° C. by a heat exchanger to obtain a moisturizing cream.

TABLE 6

| | Moisturing cream | Invention Product 7 | Invention Product 8 | Comparative Product 8 |
| --- | --- | --- | --- | --- |
| Composition (%) | 1) Silicone ester derivative (I) (Ex. 13) | 8.0 | — | — |
| | 2) Silicone ester derivative (I) (Ex. 14) | — | 8.0 | — |
| | 3) Liquid paraffin | — | — | 8.0 |
| | 4) Bees wax | 2.0 | 2.0 | 2.0 |
| | 5) Stearyl alcohol | 3.0 | 3.0 | 3.0 |
| | 6) Stearic acid | 5.0 | 5.0 | 5.0 |
| | 7) Squalane | 7.0 | 7.0 | 7.0 |
| | 8) Polyoxyethylene oetyl ether (20 E.O.) | 1.0 | 1.0 | 1.0 |
| | 9) Propylene glycol | 8.0 | 8.0 | 8.0 |
| | 10) Glycerol | 4.0 | 4.0 | 4.0 |
| | 11) Triethanolamine | 1.0 | 1.0 | 1.0 |
| | 12) Methyl paraben | 0.1 | 0.1 | 0.1 |
| | 13) Butyl paraben | 0.1 | 0.1 | 0.1 |
| | 14) Perfume | 0.1 | 0.1 | 0.1 |
| | 15) Purified water | Balance | Balance | Balance |
| Feel on Use | Moistness | Yes (moistened) | Yes | slightly moistened |
| | Stickiness | No | No | Yes (sticky) |
| | Smoothness | Yes (smooth) | Yes | No |
| | Effectiveness for chapped skin | Yes (effective) | Yes | slightly effective |

EXAMPLE 29

Cold Cream

The tetrahydroabietic ester derivative (I) obtained in Example 1 was used for preparing a cold cream.

Composition

| | |
| --- | --- |
| 1) Tetrahydroabietic ester derivative (Example 1) | 5.0 wt % |
| 2) Silicone oil | 5.0 |
| 3) Liquid paraffin | 10.0 |
| 4) Bees wax | 3.0 |
| 5) Lanolin | 1.5 |
| 6) Polyoxyethylene sorbitan monooleate | 3.0 |
| 7) Sorbitan monooleate | 2.0 |

-continued

| | |
| --- | --- |
| 8) Methyl paraben | 0.1 |
| 9) Buthyl paraben | 0.1 |
| 10) Perfume | 0.2 |
| 11) Purified water | Balance |

Preparation

Ingredients 1) to 7) and 9) were mixed at 70° C. and then added with a 70° C. mixture of 8) and 11) under stirring to obtain an emulsion. The emulsion was allowed to cool down to about 40° C., to which ingredient 10) was added to obtain a cream. This cream has notable extendability and fittability on the skin, and was suitable as a cold cream.

EXAMPLE 30

Creamy Foundation

The tetrahydroabietic ester derivative (I) obtained in Example 1 was used for preparing a creamy foundation having the following composition.

Composition

| | |
| --- | --- |
| 1) Tetrahydroabietic ester derivative (Example 1) | 1.5 wt % |
| 2) Polyoxyethylene stearate | 2.5 |
| 3) Isopropyl myristate | 6.0 |
| 4) Stearic acid | 5.0 |
| 5) Talc | 12.0 |
| 6) Titanium oxide | 5.0 |
| 7) Red ion oxide | 0.5 |
| 8) Methyl paraben | 0.1 |
| 9) Propyl paraben | 0.1 |
| 10) Perfume | 0.2 |

EXAMPLE 31

Toilet Lotion

The tetrahydroabietic ester derivative (I) obtained in Example 1 was used for preparing a toilet lotion having the following composition.

Composition

| | | |
|---|---|---|
| 1) | Tetrahydroabietic ester derivative (Example 1) | 7.0 wt % |
| 2) | Glycine | 1.0 |
| 3) | Sodium pyrrolidonecarboxylate | 1.0 |
| 4) | Glycerol | 10.0 |
| 5) | Polyoxyethylene oetyl ether | 1.5 |
| 6) | Ethanol | 10.0 |
| 7) | Perfume | 0.2 |
| 8) | Purified water | Balance |

Preparation

Ingredients 1) to 8) were mixed under stirring to obtain a substantially homogeneous solution. This toilet lotion had a good compatibility to the skin and also gave moistened feel upon use.

EXAMPLE 32

Lip Cream

The tetrahydroabietic ester derivative (I) obtained in Example 1 was used for preparing a lip cream having the following composition.

Composition

| | | |
|---|---|---|
| 1) | Tetrahydroabietic ester derivative (Example 1) | 37.0 wt % |
| 2) | Methyl-branched isostearyl glyceryl ether | 10.0 |
| 3) | Jojoba oil | 16.0 |
| 4) | Carnauba wax | 13.0 |
| 5) | Microcrystalline wax | 14.0 |
| 6) | Vaseline | 10.0 |

Preparation

Immediately after the ingredients 1) to 6) were mixed at 85° C. under stirring for homogenization, the homogenized mixture was placed in a mold and allowed to cool down. The mixture before cooling was glossy milky-white and in a semi-solid state but after shaped into a stick form, it revealed good extendability and fittability on the skin and was not easily removed off from the lip.

—continued

| | | |
|---|---|---|
| 11) | Purified water | Balance |

Preparation

Ingredients 1) to 4) and 9) were mixed at 70° C. and then added with a 70° C. mixture of 8) and 11) under stirring to obtain an emulsion. The emulsion was further blended with ingredients 5) to 7), and stirred and mixed. The mixture was cooled down to 40° C., when ingredient 10) was added thereto. The thus obtained emulsion product was resistant to perspiration and was capable retaining the make-up for a prolonged time, thus revealed excellent properties when used as a make-up foundation.

EXAMPLE 33

Moisturizing Lotion

A moisturizing lotion having the following composition was prepared by the process below.

Composition

| | | |
|---|---|---|
| 1) | Silicone ester derivative (I) of Example 6 | 1.0 wt % |
| 2) | Polyoxyethylene oleyl ether (20 E.O.) | 1.0 |
| 3) | Glycerol | 5.0 |
| 4) | 1,3-Butanediol | 5.0 |
| 5) | Polyethylene glycol 1500 | 1.5 |
| 6) | Ethanol | 10.0 |
| 7) | Methyl paraben | 0.1 |
| 8) | Perfume | Suitable amount |
| 9) | Citric acid | " |
| 10) | Sodium citrate | " |
| 11) | Purified water | Balance |
| | TOTAL | 100 |

Process

Ingredients 1), 2) 6) and 8) were mixed well, to which a mixture of 3) to 5), 7) and 9) to 11) was added and stirred to obtain a substantially homogeneous solution. This moisturizing lotion was capable of giving moistened and thick feel upon use with reduced stickiness and was excellent in moisturizing effect and sensation.

EXAMPLE 34

Milky Lotion

A milky lotion having the following composition was prepared by the process below.

Composition

| | | |
|---|---|---|
| 1) | Silicone ester derivative (I) of Example 7 | 10.0 wt % |
| 2) | Cetanol | 0.5 |
| 3) | Vaseline | 1.0 |
| 4) | Polyoxyethylene oleyl ether (20 E.O.) | 2.0 |
| 5) | Stearic acid | 2.0 |
| 6) | Glycerol | 3.0 |
| 7) | Dipropylene glycol | 5.0 |
| 8) | Triethanolamine | 1.0 |
| 9) | Ethyl paraben | 0.1 |
| 10) | Methyl paraben | 0.2 |
| 11) | Perfume | Suitable amount |
| 12) | Purified water | Balance |
| | TOTAL | 100 |

Process

Ingredients 1) to 5) were allowed to dissolve at 70° C. Similarly, ingredients 6) to 12) were heated and mixed at 70° C., to which the mixture of 1) to 5) was added. The resultant mixture was emulsified by an emulsifier, followed by cooling down to 30° C. by a heat exchanger. The milky lotion obtained gave moistened and thick feel upon use the reduced stickiness. It was excellent in moisture retainability as well as in sensation.

EXAMPLE 35

Moisturizing Lipstick

A lipstick having the following composition was prepared by the process below.

Composition

| | | |
|---|---|---|
| 1) Silicone ester derivative (I) of Ex. 8 | 25.0 wt % |
| 2) Carnauba wax | 2.0 |
| 3) Ceresine | 4.0 |
| 4) Candelilla wax | 5.0 |
| 5) Microcrystalline wax | 2.0 |
| 6) Bees wax | 5.0 |
| 7) Lanolin | 4.0 |
| 8) Castor oil | 20.0 |
| 9) Hexadecyl alcohol | 20.0 |
| 10) Glycerol | 3.0 |
| 11) Glycerol monostearate | 2.0 |
| 12) Titanium oxide | 2.0 |
| 13) Pigment (Red #202) | 2.0 |
| 14) Pigment (Red #204) | 1.0 |
| 15) Pigment (Yellow #4 Al lake) | 3.0 |
| 16) Antioxidant | Suitable amount |
| 17) Perfume | " |
| TOTAL | 100 |

Preparation

Ingredients 1) to 7), 9) and 11) were allowed to dissolve under heat, to which ingredient 10) was dropped while stirring, followed by adding with a dispersion obtained by dispersing ingredients 12) to 17) in 8) and mixed for homogenization. The resultant mixture was placed in a mold and cooled down.

This lipstick gave a moistened feel with reduced stickiness upon use, and was excellent in moisture retainability and sensation.

EXAMPLE 36

Creamy Moisturizing Foundation

A creamy moisturizing foundation having the following composition was prepared by the process below.

Composition

| | | |
|---|---|---|
| 1) Silicone ester derivative (I) of Ex. 9 | 9.0 wt % |
| 2) Stearic acid | 5.0 |
| 3) Sorbitan monostearate | 2.0 |
| 4) Cetanol | 1.0 |
| 5) Squalane | 7.0 |
| 6) Butyl paraben | 0.1 |
| 7) Triethanolamine | 1.0 |
| 8) Martitol | 2.0 |
| 9) Glycerol | 3.0 |
| 10) Methyl paraben | 0.1 |
| 11) Titanium oxide | 8.0 |
| 12) Kaolin | 5.0 |
| 13) Sericite | 2.0 |
| 14) Red iron oxide | 3.0 |
| 15) Iron (III) oxide | 2.5 |
| 16) Iron (II) oxide | 0.5 |
| 17) Perfume | Suitable amount |
| 18) Purified water | Balance |
| TOTAL | 100 |

Process

Ingredients 11) to 16) were dispersed in a homogeneous mixture of 7) to 10) and 18) and heated at 75° C., to which ingredients 1) to 6) heated at 80° C. were added under stirring for effecting emulsification, followed by cooling down to 50° C., when ingredient 17) was added, subjected to further stirring to cool it down to room temperature.

This creamy foundation gave moistened feel with reduced stickiness, and was excellent in moisture retainability and sensation.

EXAMPLE 37

W/O-type Moisturizing Cream

A w/o-type moisturizing cream having the following composition was prepared by the process below.

Composition

| | | |
|---|---|---|
| 1) Silicone ester derivative (I) of Ex. 10 | 45.0 wt % |
| 2) Paraffin | 5.0 |
| 3) Sorbitan sesquioleate | 3.0 |
| 4) Aluminum stearate | 0.5 |
| 5) Magnesium disulfide | 1.0 |
| 6) Polyethylene glycol 1500 | 2.0 |
| 7) Glycerol | 3.0 |
| 8) Polyoxyethylene methyl glucoside | 3.0 |
| 9) Perfume | Suitable amount |
| 10) Antioxidant | " |
| 11) Purified water | Balance |
| TOTAL | 100 |

Process

Ingredients 5) to 8), 10) and 11) were mixed at 70° C. Similarly, ingredients 1) to 4) were mixed at 70° C., to which the mixture of 5) to 8), 10) and 11) was added. The resultant mixture was emulsified by an emulsifier, added with 9) and stirred for homogenization. The resultant emulsion was cooled down to 30° C. by a heat exchanger to obtain a w/o moisturizing cream. The cream obtained gave moistened and thick feel upon use with reduced stickiness. It was excellent in moisture-retaining ability as well as feel on use.

EXAMPLE 38

Hand Cream

The silicone tetrahydroabietic ester derivative obtained in Example 11 was used to prepare an emulsion having the following composition.

Composition

| | | |
|---|---|---|
| 1) Silicone tetrahydroabietic ester derivative of Ex. 11 | 5.0 wt % |
| 2) Stearic acid | 10.0 |
| 3) Stearic acid monoglyceride | 1.5 |
| 4) Polyoxyethylene monostearate | 1.5 |
| 5) Triethanolamine | 0.3 |
| 6) Methyl paraben | 0.1 |
| 7) Butyl paraben | 0.1 |
| 8) Perfume | 0.2 |
| 9) Purified water | Balance |

Process

Ingredients 1) to 4) were mixed at 70° C., to which a 70° C. mixture of 5) to 7) and 9) was added under stirring for effecting emulsification. The resultant mixture was cooled down to 40° C., to which ingredient 8) was added to obtain a white emulsion. This emulsion had good fittability on the skin, and was hard to be removed by hand-washing, revealing excellent properties as a hand cream.

EXAMPLE 39

Facial Pack

The silicone tetrahydroabietic ester derivative obtained in Example 11 was used to prepare a mixture having the following composition.

Composition

| | |
|---|---|
| 1) Silicone tetrahydroabietic ester derivative of Ex. 11 | 2.5 wt % |
| 2) Polyvinyl alcohol | 15.0 |
| 3) Titanium oxide | 5.0 |
| 4) Ethylene glycol | 4.0 |
| 5) Methyl paraben | 0.1 |
| 6) Perfume | 0.2 |
| 7) Purified water | Balance |

Process

Ingredient 7) was heated at about 90° C., to which ingredient 2) was added under stirring by small amounts and allowed to dissolve until homogeneous solution was obtained. Ingredients 1) and 3) to 5) were further added thereto and stirred for homogenization. After cooling down to about 40° C., ingredient 6) was added and mixed. The obtained mixture, when used as a facial pack, gave moderate stimulation to the skin when peeled off from the facial skin and gave a prolonged moisturized feeling.

EXAMPLE 40

Lip Cream

The silicone tetrahydroabietic ester derivative obtained in Example 11 was used to prepare a mixture having the following composition.

Composition

| | |
|---|---|
| 1) Silicone tetrahydroabietic ester derivative of Ex. 11 | 10.0 wt % |
| 2) Liquid paraffin | 37.0 |
| 3) Jojoba oil | 16.0 |
| 4) Carnauba wax | 13.0 |
| 5) Microcrystalline wax | 14.0 |
| 6) Vaseline | 10.0 |

Process

Immediately after the ingredients 1) to 6) were mixed at 85° C., under stirring for homogenization, the homogenized mixture was placed in a mold and allowed to cool down. The mixture before cooling was glossy milky-white and in a semi-solid state but after shaped in to a stick form, it revealed good extendability and fittability on the skin and was not easily removed off from the lip.

EXAMPLE 41

Lotion

The silicone tetrahydroabietic ester derivative obtained in Example 11 was used to prepare a mixture having the following composition.

Composition

| | |
|---|---|
| 1) Silicone tetrahydroabietic ester derivative of Ex. 11 | 5.0 wt % |
| 2) Ethanol | 15.0 |
| 3) L-Serine | 1.0 |
| 4) Sodium pyrrolidone carboxylate | 1.0 |
| 5) Polyoxyethylene oleyl ether | 1.5 |
| 6) Perfume | 0.2 |
| 7) Purified water | Balance |

Process

Ingredients 1) to 7) were mixed under stirring for homogenization. The thus obtained lotion revealed a good fittability on the skin and gave moistened feel on use.

Example 42

Moisturizing Lotion

A moisturizing lotion having the following composition was prepared by the process below.

| | |
|---|---|
| 1) Silicone ester derivative (I) of Ex. 15 | 1.0 wt % |
| 2) Polyoxyethylene oleyl ether (20 E.O.) | 1.5 |
| 3) Glycerol | 5.0 |
| 4) 1,3-Butanediol | 5.0 |
| 5) Polyethlene glycol 1500 | 1.5 |
| 6) Ethanol | 10.0 |
| 7) Methyl paraben | 0.1 |
| 8) Perfume | Suitable amount |
| 9) Citric acid | " |
| 10) Sodium citrate | " |
| 11) Purified water | Balance |
| TOTAL | 100.0 |

Process

Ingredients 1), 2), 6) and 8) were mixed well, to which mixture of 3) to 5), 7) and 9) to 11) was added and stirred to obtain a substantially homogeneous solution. This moisturizing lotion was capable of giving moistened and thick feel upon use with reduced stickiness and was excellent in moisturizing effect and sensation.

EXAMPLE 43

Milky Lotion

A milky lotion having the following composition was prepared by the process below.

Composition

| | |
|---|---|
| 1) Silicone ester derivate (I) of Ex. 16 | 10.0 wt % |
| 2) Cetanol | 0.5 |
| 3) Vaseline | 1.0 |
| 4) Polyoxyethylene oleylether (20 E.O.) | 2.0 |
| 5) Stearic acid | 2.0 |
| 6) Glycerol | 3.0 |
| 7) Dipropylene glycol | 5.0 |
| 8) Triethanolamine | 1.0 |
| 9) Ethyl paraben | 0.1 |
| 10) Methyl paraben | 0.2 |
| 11) Perfume | Suitable amount |
| 12) Purified water | Balance |
| TOTAL | 100.0 |

Process

Ingredients 1) to 5) were allowed to dissolve under heat, and the temperature was maintained at 70° C. Ingredients 6) to 10) and 12) were also mixed at 70° C., to which the mixture of 1) to 5) was added. The obtained mixture was charged in an emulsifier for emulsification. The resultant emulsion was cooled down to 40° C. and added with ingredient 11) and mixed. A heat exchanger was used to cool down the resultant mixture to 30° C. to obtain a milky lotion.

This milky lotion gave moistened and thick feel upon use with reduced stickiness. It was excellent in moisture-retaining ability and feel on use.

EXAMPLE 44

Moisturizing Cream

A moisturizing cream having the following composition was prepared by the process below.

Composition

| | | |
|---|---|---|
| 1) Silicone ester derivative (I) of Ex. 17 | 8.0 wt % | |
| 2) Silicone ester derivative (I) of Ex. 18 | 2.0 | |
| 3) Paraffin | 2.0 | |
| 4) Cetyl 2-ethylhexanoate | 5.0 | |
| 5) Lanolin | 5.0 | |
| 6) Bees wax | 2.0 | |
| 7) Stearyl alcohol | 4.0 | |
| 8) Self-emulsified glyceryl monostearate | 1.5 | |
| 9) Polyoxyethylene sorbitan monooleate (20 E.O.) | 1.0 | |
| 10) Glycerol | 5.0 | |
| 11) 70% Soribtol | 10.0 | |
| 12) Ethyl paraben | Suitable amount | |
| 13) Methyl paraben | " | |
| 14) Perfume | " | |
| 15) Purified water | Balance | |
| TOTAL | 100.00 | |

Process

Ingredients 1) to 9) were allowed to dissolve under heat, and the temperature was maintained at 70° C. In the same manner, ingredients 10to 13) and 15) were heated at 70° C. and mixed, to which the mixture of 1) to 9) was added. The obtained mixture was charged in an emulsifier for emulsification. The resultant emulsion was cooled down to 40° C. under stirring, to which ingredient 14) was further added and mixed well. A heat exchanger was used to cool down to 30° C. to obtain a moisturizing cream.

This moisturizing cream was excellent in moisture retainability and feel on use, giving moistened feel with reduced stickiness.

EXAMPLE 45

Cold Cream

A cold cream having the following composition was prepared by the process below.

Composition

| | | |
|---|---|---|
| 1) Silicone ester derivative (I) of Ex. 19 | 28.0 wt % | |
| 2) Silicone ester derivative (I) of Ex. 20 | 2.0 | |
| 3) Bees wax | 5.0 | |
| 4) Spermaceti | 3.0 | |
| 5) Cetyl 2-ethylhaxnoate | 10.0 | |
| 6) Cetanol | 1.0 | |
| 7) Self-emulsified glyceryl monostearate | 7.0 | |
| 8) Polyoxyethylene sorbitan monooleate (20 E.O.) | 2.0 | |
| 9) Glycerol | 5.0 | |
| 10) Triethanolamine | 0.3 | |
| 11) Ethyl paraben | Suitable amount | |
| 12) Methyl paraben | " | |
| 13) Perfume | " | |
| 14) Purified water | Balance | |
| TOTAL | 100.0 | |

Process

Ingredients 1) 8) was allowed to dissolve under heat, and temperature was maintained at 70° C. In the same manner, ingredients 9) to 12) and 14) were heated at 70° C. and mixed, to which the mixture of 1) to 8) was slowly added. The obtained mixture was charged in an emulsifier for emulsification. The resultant emulsion was cooled down to 40° C. under stirring to which ingredient 13) was further added and mixed well. A heat exchanger was used to cool down to 30° C. to obtain a cold cream.

This cold cream was excellent in moisture retainability and feel on use giving thick and moistened feel with reduced stickiness.

EXAMPLE 46

Creamy Moisturizing Foundation

A creamy moisturizing foundation having the following composition was prepared by the process below.

Composition

| | | |
|---|---|---|
| 1) Silicone ester derivative (I) of Ex. 21 | 10.0 wt % | |
| 2) Liquid paraffin | 8.0 | |
| 3) Squalane | 8.0 | |
| 4) Neopentyl glycol dioctanoate | 3.0 | |
| 5) Sorbitan sesqui isostearate | 7.0 | |
| 6) Aluminum distearate | 0.2 | |
| 7) Magnesium sulfate | 0.7 | |
| 8) Martitol | 2.0 | |
| 9) Glycerol | 3.0 | |
| 10) Methyl paraben | 0.1 | |
| 11) Titanium oxide | 8.0 | |
| 12) Talc | 5.0 | |
| 13) Sericite | 2.0 | |
| 14) Red iron oxide | 0.4 | |
| 15) Iron (III) oxide | 0.7 | |
| 16) Iron (II) oxide | 0.1 | |
| 17) Perfume | Suitable amount | |
| 18) Purified water | Balance | |
| TOTAL | 100.0 | |

Process

Ingredients 1) to 6) were heated at 70° C. and mixed well. In this homogeneous mixture, ingredients 11) to 16) were dispersed, to which a homogeneous mixture of ingredients 7) to 10) and 18) heated at 70° C. were added under stirring for effecting emulsification. The emulsion was cooled down to 40° C. under stirring, when 17) was further added and cooled to room temperature under stirring.

This creamy foundation gave moistened feel with reduced stickiness, and was excellent in moisture retainability and sensation.

EXAMPLE 47

Moisturizing Lipstick

A moisturizing lipstick having the following composition was prepared by the process below.

Composition

| | | |
|---|---|---|
| 1) Silicone ester derivative (I) of Ex. 22 | 20.0 wt % | |
| 2) Silicone ester derivative (I) of Ex. 23 | 5.0 | |
| 3) Carnauba wax | 2.0 | |
| 4) Ceresine | 4.0 | |
| 5) Candelilla wax | 5.0 | |
| 6) Microcrystalline wax | 2.0 | |
| 7) Bees wax | 5.0 | |
| 8) Lanoline | 4.0 | |
| 9) Castor oil | 20.0 | |
| 10) Hexadecyl alcohol | 20.0 | |
| 11) Glycerol | 3.0 | |
| 12) Glycerol monostearate | 2.0 | |
| 13) Titanium oxide | 2.0 | |
| 14) Pigment (Red #202) | 2.0 | |

-continued

| | | |
|---|---|---|
| 15) Pigment (Red #204) | | 1.0 |
| 16) Pigment (Yellow #4 Al lake) | | 3.0 |
| 17) Antioxidant | | Suitable amount |
| 18) Perfume | | " |
| TOTAL | | 100.0 |

Process

Ingredients 1) to 8), 10) and 12) were allowed to dissolve under heat, to which ingredient 11) was dropped while stirring, followed by adding with a dispersion obtained by dispersing ingredients 13) to 18) in 9) and mixed for homogenization. The resultant mixture was placed in a mold and cooled down.

This lipstick gave a moistened feel with reduced stickiness upon use, and was excellent in moisture retainability and sensation.

EXAMPLE 48

Nail Enamel Remover

A nail enamel remover having the following composition was prepared by the process below.

Composition

| | |
|---|---|
| 1) Acetone | 60.0 wt % |
| 2) Butyl acetate | 30.0 |
| 3) 1,3-Butanediol | 2.0 |
| 4) Silicone ester derivate (I) of Ex. 23 | 1.0 |
| 5) Dye | Suitable amount |
| 6) Perfume | " |
| 7) Purified water | Balance |
| TOTAL | 100.0 |

Process

Ingredients 1) to 7) were homogeneously mixed to prepare a nail enamel remover. This remover was excellent in feel on use.

What is claimed is:

1. A cosmetic composition comprising a cosmetically effective amount of an alcohol-modified silicone ester derivative of the following formula (I):

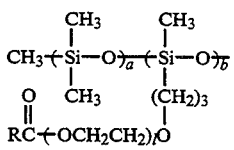

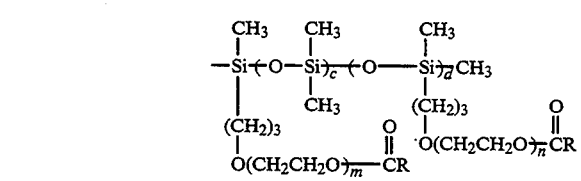

wherein

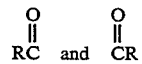

are selected from the group consisting of an abietic acid residue, a dehydroabietic acid residue, a dihydroabietic acid residue and a tetrahydroabietic acid residue; a, b and c are numbers which sum falls in the range from 0 to 90; d is 0 or 1; a, b, c and d are not all 0 at the same time, l, m and n are numbers which sum falls in the range from 0 to 6, and each of l, m and n being 0 to 2.

2. The cosmetic composition according to claim 1, further comprising a polyol-type in a moisturizing effective amount.

3. The cosmetic composition according to claim 1, comprising 0.001 to 90% wt. of the total composition of said alcohol-modified silicone ester derivative.

4. The cosmetic composition according to claim 2, wherein the polyol-type moisturizer is present in an amount of 2–90% wt. based on the total amount of the composition.

* * * * *